United States Patent [19]

Lyon et al.

[11] 4,027,661
[45] June 7, 1977

[54] PRESSURE SENSOR
[75] Inventors: Warren Charles Lyon, Baltimore; William H. Hayes, Jr., Woodbine, both of Md.
[73] Assignee: Hittman Corporation, Columbia, Md.
[22] Filed: July 16, 1974
[21] Appl. No.: 488,988
[52] U.S. Cl. .................. 128/2 A; 73/393; 73/410; 128/2.05 D; 128/2.05 E; 250/336
[51] Int. Cl.² .......................... A61B 5/00
[58] Field of Search ......... 128/2 A, 2.05 D, 2.05 E, 128/350 R, 350 V, 1 R; 73/406, 407, 409–412, 418, 393; 250/336 R

[56] References Cited
UNITED STATES PATENTS

| 3,034,356 | 5/1962 | Bieganski et al. | 128/2.05 E |
| 3,503,402 | 3/1970 | Schulte | 128/350 V |
| 3,625,199 | 12/1971 | Summers | 128/2.05 E |
| 3,686,958 | 8/1972 | Porter et al. | 73/406 |
| 3,789,667 | 2/1974 | Porter et al. | 73/406 |

Primary Examiner—Kyle L. Howell
Attorney, Agent, or Firm—Fleit & Jacobson

[57] ABSTRACT

A pressure sensor apparatus primarily for sensing pressure in a body cavity such as the cranium, bladder or vena cava of an animal or human comprising a housing having a bellows defining a chamber within the housing. Means is provided for communicating pressure from the body cavity to the chamber. A radioactive material is housed in the housing and at least partially surrounded by radiation shielding. The radiation shielding shields the radioactive material as a function of the pressure sensed by the flexible member and the radioactivity is sensed by a radiation detector.

23 Claims, 3 Drawing Figures

PRESSURE SENSOR

CROSS-REFERENCE TO RELATED APPLICATION

This application is related to commonly assigned application Ser. No. 478,763, filed June 12, 1974, for PRESSURE SENSOR APPARATUS, by Thomas S. Bustard et al., now abandoned.

BACKGROUND OF THE INVENTION

The need for a non-invasive technique for measuring the pressure in body cavities of animals or humans is recognized as highly desirable for continuous on intermittent monitoring of body conditions. Such cavities as the cranium, vena cava, bladder, and others provide valuable and sometimes critical information for maintaining the well being or survival of an animal or human. For example, it is known that intracranial pressure provides a valuable indication of well being for a variety of clinical conditions.

A long-term, non-invasive monitor of intracranial pressure is particularly desirable for the congenital hydrocephalic. This condition is one in which the normal production of cerebralspinal fluid is not balanced by reabsorption of the fluid. The retained fluid increases the intracranial pressure and causes head swelling which is a characteristic of hydrocephalus. The increase in intracranial pressure can eventually lead to disability or death.

The normal treatment for hydrocephalus comprises surgically implanting a fluid shunt to transfer cerebrospinal fluid from the intracranial cavity to other parts of the body such as the peritoneal cavity or the jugular vein. The surgically implanted shunt is basically a drainage tube which contains a check valve and requires a modest pressure differential for the cerebrospinal fluid to flow. These shunts often become partially or even fully blocked and intracranial pressure starts to rise resulting in intracranial hypertension.

The symptoms characteristic of a blocked shunt are also characteristic of various other maladies. Early symptoms of a clogged shunt are nausea, headache, and dizziness, any of which can result from many other causes other than intracranial hypertension. In young children especially a physician cannot easily determine shunt blockage without performing a surgical procedure. The presence of an indwelling pressure sensor would permit the physician to directly monitor the intracranial pressure and remove a substantial amount of the risk from his diagnosis.

An additional problem associated with a blocked vent is the rate at which the pressure can rise. Drastic increases can occur within less than an hour. Since a high pressure that is maintained for a period of time will cause irreversible brain damage, it is imperative that pressure increases be discovered in the shortest possible time. Full utilization of a pressure sensor requires a simplified determination of the pressure so that even a parent can perform the determination.

Against this background, there is a recognized and long felt need for a device which overcomes the aforementioned disadvantages and provides a sensor having a self-contained, long-term energy source with compensation for ambient pressure variations and low sensitivity to temperature changes.

The pressure sensor of the present invention is designed to eliminate many of the previously mentioned problems. Once the pressure sensor is installed by a competent surgeon, the pressure can be read non-invasively by a physician with a minimal amount of special equipment. If an attending physician is not readily available, equipment can be installed in the child's home and the parents instructed in its use.

SUMMARY OF THE INVENTION

The pressure sensor of the present invention is fully implantable and contains a radioactive material so that the pressure can be readout non-invasively. In its preferred form, the sensor system comprises a housing having a chamber defined therein by a resilient bellows. Non-radioactive fluid is contained in the chamber and is in communication with a flexible member placed in the body cavity and exposed to the pressure to be sensed. The housing is located external to the cavity being sensed and preferably situated just under the skin. The housing contains a radioactive material at least partially surrounded by radioactive shielding. Either the radioactive material or the radioactive shielding is connected to the bellows. The pressure acting upon the flexible member causes the bellows to expand and contract. The movement of the bellows causes the radioactive shielding to shield the radioactive material as a function of the pressure sensed. The radioactivity is sensed from outside the skin by a conventional nuclear counter or crystal detector instrument.

The application of the present invention to hydrocephalus greatly facilitates treatment of the defect. The pressure sensor of the present invention when used as an intracranial pressure sensor device has a long life, is fully implantable and does not require any energy source other than the radioactive material contained in the device. Two of the major advantages of the present invention are the elimination of implanted energy sources, such as batteries, to operate the device, and the elimination of leads or other penetrations through the skin to provide power or transmit a signal. With a long-lived radioisotope such as promethium 145, the inventive pressure sensing device can be fully implanted and left in place for the life of the patient. Furthermore, the invention comprises a design and a selection of materials that will assure a negligible radiation dosage to the patient. Although in this application, the invention is primarily intended for a long-term implantation in hydrocephalic children, one may easily appreciate its value in short-term monitoring of head trauma patients.

The inventive pressure monitoring system can be fully implanted with no tubing or wires penetrating the skin, functions accurately to within several millimeters of water pressure and in unaffected by variations in ambient pressure. Also, it is generally insensitive to ambient temperature. Furthermore, the materials used to construct the devices according to the present invention are biologically inert and do not pose any health hazard to the animal or human subject or make the subject more susceptible to mechanical trauma. The sensor unit is of relatively small size and so does not produce unsightly bulging when implanted subdermally.

Other features and advantages of the invention will be apparent from the following description of the preferred embodiments of the invention as shown in the accompanying drawings.

DESCRIPTION OF THE PREFERRED EMBODIMENTS

Figure 1:
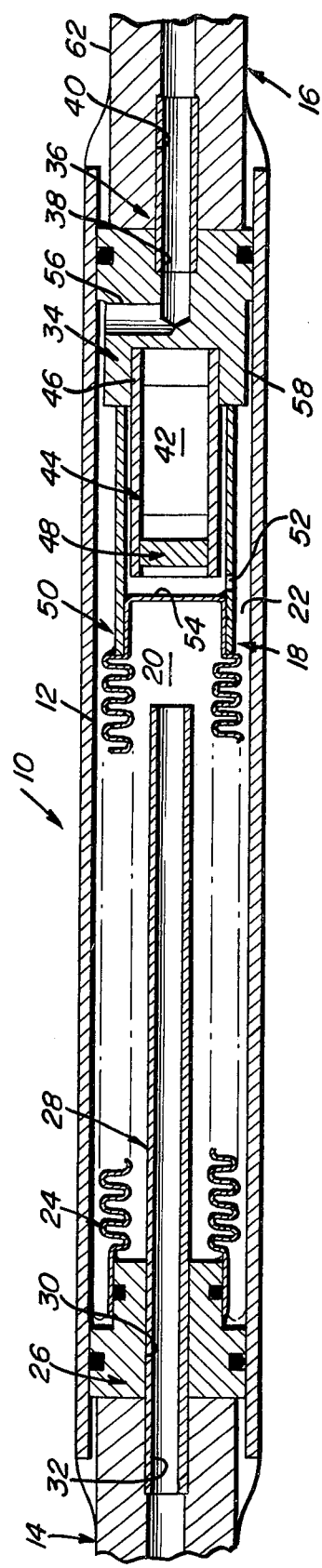
FIG. 1 is a vertical, cross-sectional view of one embodiment of the pressure sensor apparatus of the present invention.

Pressure sensor 10 broadly comprising housing 12 and flexible containers or tambours 14 and 16. Housing 12 defines an interior opening 18 which is divided into two chambers 20 and 22, respectively, by bellows 24. Chambers 20 and 22 act as reservoirs for non-radioactive fluid.

Bellows support 26 is mounted in the end of housing 12 and closes chamber 20. Chamber 20 is fluidly connected to tambour 14 by means of bellows tube 28 which fits into port 30 of bellows support 26 and opening 32 in the end of tambour 14. Chamber 22 is closed by radioactive material tube support 34 which is mounted in the other end of housing 12 from bellows support 26. Chamber 22 is fluidly connected to tambour 16 by means of connection tube 36 which fits into port 38 in radioactive material tube support 34 and into opening 40 in the end of tambour 16.

The radioactive material 42 is housed in source tube 44 which is mounted in opening 46 in radioactive material tube support 34. The open end of source tube 44 is closed by shield plug 48. Surrounding source tube 44 is shield tube 50 which is connected to bellows 24. Opening 52 in shield tube 50 places the face 54 of bellows 24 in communication with tambour 16 through port 56 in the body of radioactive material tube support 34 and annular opening 58 formed between housing 12 and radioactive material tube support 34.

Figure 2:
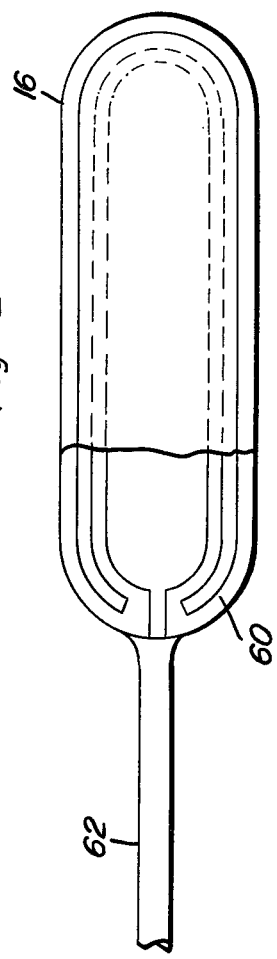
FIG. 2 is a plane view, partly in section, of one of the flexible tambours a portion of which is shown in FIG. 1.

Tambour 16 is filled with a non-radioactive fluid and is placed in the body cavity such as the cranium, bladder, on vena cava of an animal or human for sensing the pressure of the body cavity. Tambour 16 must be constructed of a flexible material so that it will be responsive to pressure changes and a material which is impermeable to the non-radioactive fluid and in particular to water. A desirable material from the standpoint of flexibility and tissue compatibility is silicone rubber such as the elastomer sold under the trademark Silastic. However, extensive experimentation has shown that silicone rubber tambours cannot be used because of loss of fluid through the wall of the tambour. It was recently discovered that butyl rubber when has a low diffusion coefficient for water is a suitable material from which the tambour can be fabricated. This discovery is disclosed and claimed in the commonly assigned application cross-referenced above. The butyl rubber tambour can be coated with a thin coating of silicone rubber to provide better tissue compatibility. Tambour 16 is essentially a flexible container or sack which can be formed in any suitable shape such as cylindrical, disc-shaped, spheroidal or planar. As shown in FIG. 2, wire 60 can be placed in tambour 16 to give it suitable shape. Furthermore, a coiled spring (not shown) can be placed in neck portion 62 of tambour 16.

Sensor 10 is preferably constructed so that it is only responsive to pressure changes in the body cavity being sensed and is not responsive to ambient pressure changes. Tambour 14, which can be the same as tambour 16, provides this function and is filled with the same non-radioactive fluid as tambour 16. Accordingly, changes in ambient pressure will be exerted equally on both flexible tambours 14 and 16 making sensor 10 responsive only to changes in body cavity pressure sensed by tambour 16. Optionally, tambour 14 can be eliminated, the end of bellows tube 28 sealed, and chamber 20 filled with gas or evacuated to indicate absolute pressure. Also, for certain applications, tube 28 can be left open to communicate with the atmosphere.

Housing 12 as well as bellows support 26 and tubes 28, 40 and 44 are preferably constructed of titanium. Bellows 24 is preferably constructed of nickel and typically has a spring rate of 0.10 lbs/in. Radioactive material tube support 34, shielding plug 48 and shielding tube 50 preferably comprises tantalum shielding; however, tungsten, iridium, rhenium, platinum, rhodium, gold, or other suitable heavy metals can be used. All tubing, housing and diaphragm joints are suitably formed by epoxies, brazing, or the use of suitable gaskets, etc. Finally, the entire sensor can be coated with a thin coating of silicone rubber or placed in a silicone rubber boot if desired to assure tissue compatibility.

Changes in pressure of the body cavity being monitored compress tambour 16 and cause fluid to flow from tambour 16 through tubing 36 and into chamber 22 in housing 12. Tambour 16 offers effectively no resistance to the pressure change because of its flexible construction. Housing 12 provides a mechanical interface between the non-radioactive, pressure sensing fluid in tambour 16 and the ambient pressure compensating, non-radioactive fluid in tambour 14. Bellows 24 separates the two fluids and provides the force necessary to balance the body cavity pressure. As bellows 24 contracts under increasing body cavity pressure, it moves shielding tube 50 away from radioactive tube support 34. Since the count rate is directly dependent on the degree of shielding of radioactive material 42, the body cavity pressure can immediately be determined via the count rate.

Because of the unique construction of pressure sensor 10, no external leads are required and the sensor occupies very little space under the scalp so that it produces only a slight elevation thereof when the sensor is used for sensing intracranial pressure. Tambour 16 is placed through a burr hole within the skull and housing 12 is positioned outside the skull, but implanted under the scalp. A change in the volume of non-radioactive fluid in housing 12 is detected by measuring the change in radioactivity immediately adjacent to the skin caused by the movement of shielding tube 50. Thus, the skin does not have to be penetrated to obtain reliable pressure information. The quantity of the radioisotope utilized in the device is extremely small, typically less than one microcurie and results in surface dose rates to the scalp and skull which are on the order of 100 times less than the rates necessary to cause detectable changes in the most radiosensitive body tissue and thus will not adversely affect the adjacent skin or bone marrow.

The radioisotope used in the present invention should have a half life which is sufficiently long to give acceptable end-of-life pressure data. The radioisotope should also be safe as a source of radiation when used immediately beneath the scalp or within a body cavity. Another requirement is that the radioisotope must be detected efficiently which means it must have a high skin transmissibility as well as a high detector efficiency.

The preferred radioisotope used in the present invention is promethium 145. Promethium has an 18 year half life and a soft gamma emission which can be easily transmitted through the skin and efficiently detected while being safely used in quantities necessary for statistical counting accuracy. Among other radioisotopes which can be used in the invention is holmium 163 which has a 40 to 60 year half life. The radioisotope is preferably mixed in an epoxy binder so that a solid radioactive material can be used.

Figure 3:
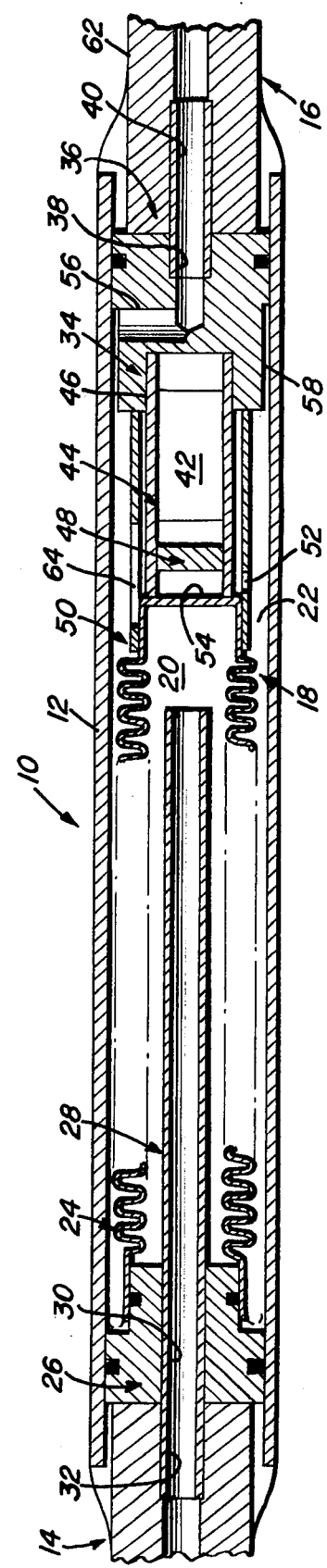
FIG. 3 is a vertical, cross-sectional view of a second embodiment of the pressure sensor apparatus of the present invention.

While the pressure sensor of the present invention has been illustrated primarily as an intracranial pressure sensor, it should be understood that the sensor is also useful in other body cavities in the treatment or care of animals and humans. Thus, valuable information may be derived from monitoring pressure in the vena cava, bladder, or some other body cavity. Further, use of the sensor is also applicable to determination of pressure difference or pressure in other applications, the foregoing details with respect to intracranial pressure being but a specific illustration of the application of the present invention to a particular problem and, in that sense, illustrative rather than limiting. Furthermore, while a preferred embodiment of the invention has been disclosed, it should be understood that the invention is not limited to such embodiment. For example, as shown in FIG. 3, source tube 44 can be connected to bellows 24 and shielding tube 50 to support 34. A window 64 can then be placed in shielding tube 50 and the count rate determined by placing a nuclear counter or crystal detector directly over the window as the radioactive material is moved by bellows 24 in reponse to pressure changes sensed by tambour 16. As a further example, tambour 16 can be replaced by a shunt tube containing a filter material which excludes particulate matter such as fibroblasts while permitting body fluid passage such as disclosed in commonly assigned application Ser. No. 489,000, filed on even date herewith, for APPARATUS FOR SENSING PRESSURE, by Glenn A. Meyer. Accordingly, the present invention should only be limited as defined in the appended claims.

What is claimed is:

1. A pressure sensor apparatus comprising a housing, resilient means defining a chamber in said housing, a non-radioactive fluid contained within said chamber, pressure communication means for placing said chamber in communication with the pressure to be sensed so that said pressure will cause said resilient means to move, a radioactive material contained within said housing and radiation shielding means at least partially surrounding said radioactive material, one of said radioactive material and said radiation shielding means being operatively connected to said resilient means and moveable therewith, said radiation shielding means shielding said radioactive material as a function of the pressure acting upon said pressure communication means.

2. The apparatus of claim 1 in which said radiation shielding means is operatively connected to said resilient means and moves as a function of the pressure acting upon said pressure communication means.

3. The apparatus of claim 1 in which said radioactive material is operatively connected to said resilient means and moves as a function of the pressure acting upon said pressure communication means.

4. The apparatus of claim 3 in which said shielding means includes a window for monitoring said radioactive material.

5. The apparatus of claim 1 in which said resilient means comprises a bellows.

6. The apparatus of claim 1 in which said pressure communication means comprises flexible means impermeable to said non-radioactive fluid.

7. The apparatus of claim 6 in which said resilient means further defines a second chamber in said housing containing a second non-radioactive fluid and said apparatus further comprises a second flexible means in communication with said second chamber.

8. The apparatus of claim 6 in which said flexible means impermeable to said non-radioactive fluid is fabricated from butyl rubber.

9. The apparatus of claim 1 in which said radioactive material is a solid.

10. The apparatus of claim 9 in which said solid is promethium 145 in an epoxy binder.

11. A pressure sensor apparatus comprising a housing, bellows means defining a chamber in said housing, flexible means in communication with said chamber, a non-radioactive liquid contained within said chamber and said flexible means so that pressure acting upon said flexible means will cause said bellows means to contract and expand, a radioactive material contained within said housing and radiation shielding means connected to said bellows means and at least partially surrounding said radioactive material, said radiation shielding means shielding said radioactive material as a function of the pressure acting upon said flexible means.

12. The apparatus of claim 11 in which said radiation shielding means is operatively connected to said resilient means and moves as a function of the pressure acting upon said first pressure sensing means.

13. The apparatus of claim 12 in which said shielding means includes a window for monitoring said radioactive material.

14. The apparatus of claim 11 in which said radioactive material is operatively connected to said resilient means and moves as a function of the pressure acting upon said first pressure sensing means.

15. An intracranial pressure sensor apparatus of the type to be positioned between the scalp and skull and having a pressure transferring mechanism extending through the skull comprising a rigid, transfer housing adapted to be positioned between the skull and scalp, resilient means mounted in said housing to divide said housing into first and second chambers, said transfer housing having inlet means connected to said first chamber and outlet means connected to said second chamber, first pressure sensing means connected at one end to said inlet means and having its other end adapted to be positioned inside the skull, a first non-radioactive fluid contained within said first pressure sensing means and said first chamber, said pressure sensing means being flexible and impermeable to said first non-radioactive fluid, second pressure sensing means connected to said outlet means and adapted to be exposed to pressure between the scalp and skull, a second non-radioactive fluid contained within said second pressure sensing means and said second chamber, said second pressure sensing means being flexible and impermeable to said second non-radioactive fluid, radioactive material contained within said transfer housing and radiation shielding means at least partially surrounding said radioactive material, one of said radioactive material and said radiation shielding means being operatively connected to said resilient means and movable therewith, whereby pressure acting upon said first pressure sensing means within the skull will cause said resilient means to move and said radiation shielding means to shield said radioactive material as a function of said pressure, said radioactive material adapted to being sensed externally of the scalp by a radiation detector, said second pressure sensing means acting to compensate for changes in ambient pressure externally of the scalp.

16. A pressure sensor apparatus comprising a housing, bellows means defining a chamber in said housing, flexible means in communication with said chamber, a non-radioactive liquid contained within said chamber and said flexible means so that pressure acting upon said flexible means will cause said bellows means to contract and expand, radiation shielding means contained within said housing and a radioactive material connected to said bellows means and being at least partially surrounded by said radiation shielding means, said radiation shielding means shielding said radioactive material as a function of the pressure acting upon said flexible means.

17. A pressure sensor for monitoring the pressure in a body cavity comprising, in combination, a housing, a radioactive source disposed within said housing, radiation shielding means associated with said housing, means for positioning said radioactive source and said radiation shielding means in a shielding relationship, pressure responsive means communicating with said housing interior for sensing the pressure in a body cavity, said pressure responsive means being arranged to transmit the pressure in said body cavity to said housing interior to change said shielding relationship between said radioactive source and said radiation shielding means as a function of the pressure in said body cavity to produce a radioactive output proportional to the pressure in said body cavity.

18. A pressure sensor for monitoring the pressure in a body cavity comprising, in combination, a housing, a radioactive source disposed within said housing, radiation shielding means associated with said housing, means for resiliently positioning said radioactive source and said radiation shielding means in a shielding relationship, pressure responsive means communicating with said housing interior for sensing the pressure in a body cavity, said pressure responsive means being arranged to transmit the pressure in said body cavity to said housing interior in opposition to the force of said positioning means for changing said shielding relationship between said radioactive source and said radiation shielding means as a function of the pressure in said body cavity to produce a radioactive output proportional to the pressure in said body cavity.

19. A pressure sensor for monitoring the pressure in a body cavity comprising, in combination, a housing having an interior, a radioactive source disposed within said housing interior, radiation shielding means disposed within said housing interior, resilient means in said housing interior for urging said radioactive source and said radiation shielding means into a shielding relationship, pressure responsive means communicating with said housing interior for sensing the pressure in a body cavity, said pressure responsive means being arranged to transmit the pressure in said body cavity to said housing interior in opposition to the force of said resilient means for changing said shielding relationship between said radioactive source and said radiation shielding means as a function of the pressure in said body cavity to produce a radioactive output from said pressure sensor proportional to the pressure in said body cavity.

20. A pressure sensor in accordance with claim 19 and further comprising ambient pressure responsive means communicating with said housing interior for transmitting ambient pressure to said resilient means in the direction of the urging force of said resilient means.

21. A pressure sensor in accordance with claim 19 wherein said pressure responsive means includes a pressure sensing device of flexible material for insertion in the body cavity and a pressure-transmitting fluid in said pressure sensing device and said housing interior for transmitting the pressure in said body cavity sensed by said pressure sensing device to said housing interior.

22. A pressure sensor in accordance with claim 21 wherein said pressure sensing device comprises a substantially planar member of flexible material having an interior and a neck portion having one end communicating with said housing interior and the other end with the interior of said planar member.

23. A pressure sensor in accordance with claim 19 wherein said resilient means comprises a bellows and wherein one of said radiation shielding means and said radioactive source are mounted on one end of said bellows.

* * * * *